United States Patent [19]

Miller

[11] Patent Number: 4,579,227

[45] Date of Patent: Apr. 1, 1986

[54] INSPECTION AND SORTING OF GLASS CONTAINERS

[75] Inventor: John W. V. Miller, Toledo, Ohio

[73] Assignee: Owens-Illinois, Inc., Toledo, Ohio

[21] Appl. No.: 605,455

[22] Filed: Apr. 30, 1984

[51] Int. Cl.$^4$ .............................................. B07C 5/342
[52] U.S. Cl. ................................... 209/526; 209/538; 209/588; 209/939; 250/223 B; 356/240; 356/428; 358/106
[58] Field of Search ................................ 209/522–524, 209/526, 538, 588, 939; 250/223 B; 356/240, 428; 358/106

[56] References Cited

U.S. PATENT DOCUMENTS

| | | | |
|---|---|---|---|
| 3,454,759 | 7/1969 | Calhoun | 209/588 X |
| 3,932,042 | 1/1976 | Faani et al. | 209/524 X |
| 4,293,219 | 10/1981 | Ducloux | 356/240 |
| 4,378,493 | 3/1983 | Dorf et al. | 250/223 B |
| 4,500,203 | 2/1985 | Bieringer | 356/240 |

*Primary Examiner*—Robert B. Reeves
*Assistant Examiner*—Edward M. Wacyra
*Attorney, Agent, or Firm*—John R. Nelson

[57] ABSTRACT

A method and apparatus for optically inspecting and sorting transparent containers such as glass containers having defects in the container sidewalls, and for distinguishing unacceptable major refractive defects and opaque defects from each other and from commercially acceptable minor refractive defects. First and second sources of diffused illumination having differing source widths are sequentially directed onto a container while the container is rotated about its central axis for at least one revolution during each illumination. A camera which includes a plurality of light sensitive elements disposed in a linear array parallel to the axis of container rotation is positioned to receive light energy transmitted through the container sidewall. Electronics monitors the camera light elements during each revolution of the container, identifies defects as a function of differences in light transmitted through the container in each of the first and second illuminations, and generates a reject signal to sort defective containers from otherwise commercially acceptable containers. A conveyor sequentially presents containers for inspection and includes separate selectable exit paths for acceptable and unacceptable containers.

13 Claims, 8 Drawing Figures

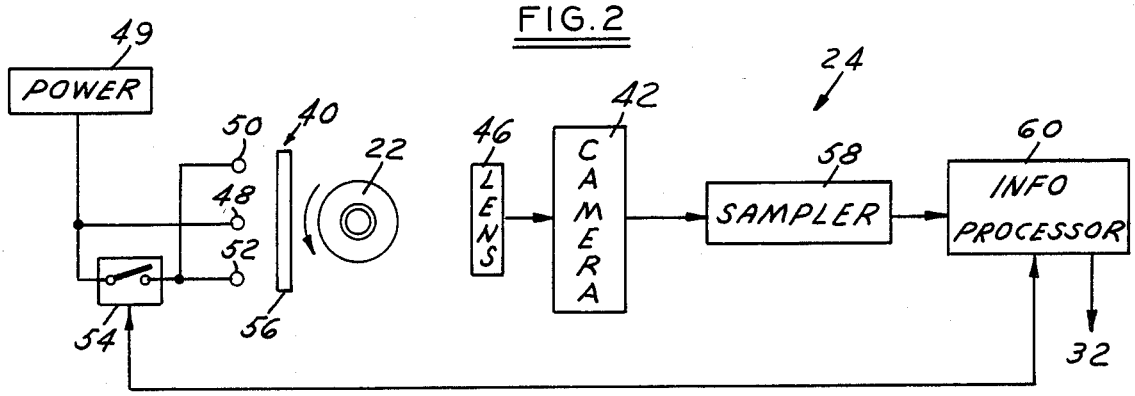
FIG. 2
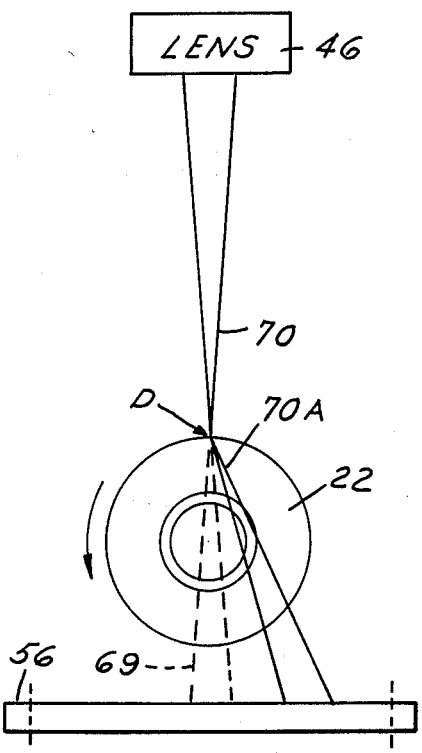
FIG. 3
FIG. 3A(1)
FIRST REVOLUTION
FIG. 3A(2)
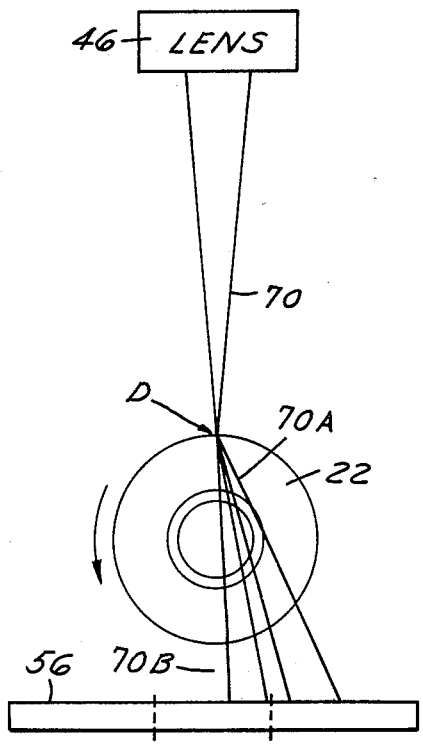
FIG. 3B(1)
SECOND REVOLUTION
FIG. 3B(2)

INSPECTION AND SORTING OF GLASS CONTAINERS

The present invention is directed to inspecting and sorting of transparent containers for defects in the container sidewalls; and more particularly to inspection of glass containers for refractive sidewall defects such as blisters and/or opaque sidewall defects such as stones, and selective sorting of containers having defects so detected.

BACKGROUND OF THE INVENTION

In the manufacture of glass containers, various types of defects may occur. It has heretofore been proposed to utilize optical scanning techniques for inspecting such containers for defects which affect optical transmission characteristics of the container sidewall. In U.S. Pat. Nos. 4,378,493, 4,378,494 and 4,378,495, all of which are assigned to the assignee of the present application, there is disclosed a method and apparatus in which glass containers are conveyed through a plurality of positions or stations where they are physically and optically inspected. At one optical inspection station, a glass container is held in vertical orientation and rotated about its vertical central axis. A light source directs wide angle diffused light energy through the container sidewall. A camera, which includes a plurality of light sensitive elements, i.e., pixels, oriented in a linear array parallel to the vertical axis of container roation, is positioned to view light transmitted through a vertical strip of the container sidewall. The output of each light sensitive element is sampled at increments of container rotation, and event signals are generated when the magnitude of adjacent pixel signals differs by more than a preselected threshold level. An appropriate reject signal is thus produced and the defective container is sorted from the conveyor line.

The method and apparatus disclosed in the aforementioned patents, commonly referred to as the Sidewall Inspection Device (SID), have been found to be very effective and efficient for automated inspection and sorting of glass containers. The present SID employs a wide source of light energy. The source is wide enough so that most refractive defects do not refract the light enough to be visible as a dark spot on the bright background of the wide source. However, because opaque defects absorb or block transmission of light energy, they are visible as dark spots on a bright background. In other words, the present SID detects opaque defects, but is blind to many refractive defects. An "event" signal will be associated with the dark spot when the magnitudes of adjacent pixel signals differ by more than a predetermined threshold. The event occurs at a specific "location" on the sidewall of a container. The event location is defined by the angular position of the container and the pixel number on the linear array which corresponds to the longitudinal position of the defect along container sidewall. The present SID also performs a connectivity analysis by evaluating the locations of a plurality of events to determine whether an opaque defect is present. For example, a tight grouping of events would indicate the presence of an opaque defect, whereas a loose grouping of events would not.

OBJECTS AND SUMMARY OF THE INVENTION

It is therefore an object of the present invention to provide an improved method and apparatus for inspecting and sorting transparent containers, particularly glass containers, which are economical to implement, which embody the proven technology disclosed in the aforementioned patents and application, which are capable of readily distinguishing character and size of sidewall defects, and which are effective for sorting containers having commercially unacceptable defects while passing containers having commercially acceptable defects.

The instant invention is directed to the problem of identifying and categorizing refractive defects. This is accomplished by spinning the container twice in order to gather two sets of data, one set during the first revolution and the other during the second. The first revolution corresponds in operation to that of the present SID as just described. If it is determined that an opaque defect is present, the container is rejected. If, on the other hand, it is determined during the first scan that the container contains no opaque defects, data gathered during the second revolution, which uses a narrower source of light energy, is examined. Most refractive defects which were not detectable during the first revolution are detectable during the second revolution because the narrower source has a width that is small enough so that they become visible as dark spots because the defect refracts the view of a pixel outside the width of the narrow source. Thus, all events produced by dark spots during the second revolution correspond to refractive defects since it has already been determined that the events produced in the first revolution did not, when analyzed, indicate the presence of an opaque defect. Another connectivity analysis is then conducted on the data gathered during the second revolution wherein the size-threshold of the event groupings is increased so that several small refractive defects can be distinguished from a large refractive defect. The presence of several small refractive defects is commercially acceptable and would not require rejection of the container, whereas the presence of a large refractive defect would require that the container be rejected.

DESCRIPTION OF THE DRAWINGS

FIG. 2 is an electrical and optical functional block diagram of a preferred embodiment of the invention.

FIG. 3A(1) and 3B(1) are schematic drawings, and FIGS. 3A(2) and 3B(2) are graphic illustrations, which together illustrate operation of the embodiment of FIG. 2.

DESCRIPTION

The disclosures of the above-noted U.S. Pat. Nos. 4,378,493, 4,378,494 and 4,378,495, all issued Mar. 29, 1983 to the assignee of the present application, are incorporated herein by reference.

Figure 1:
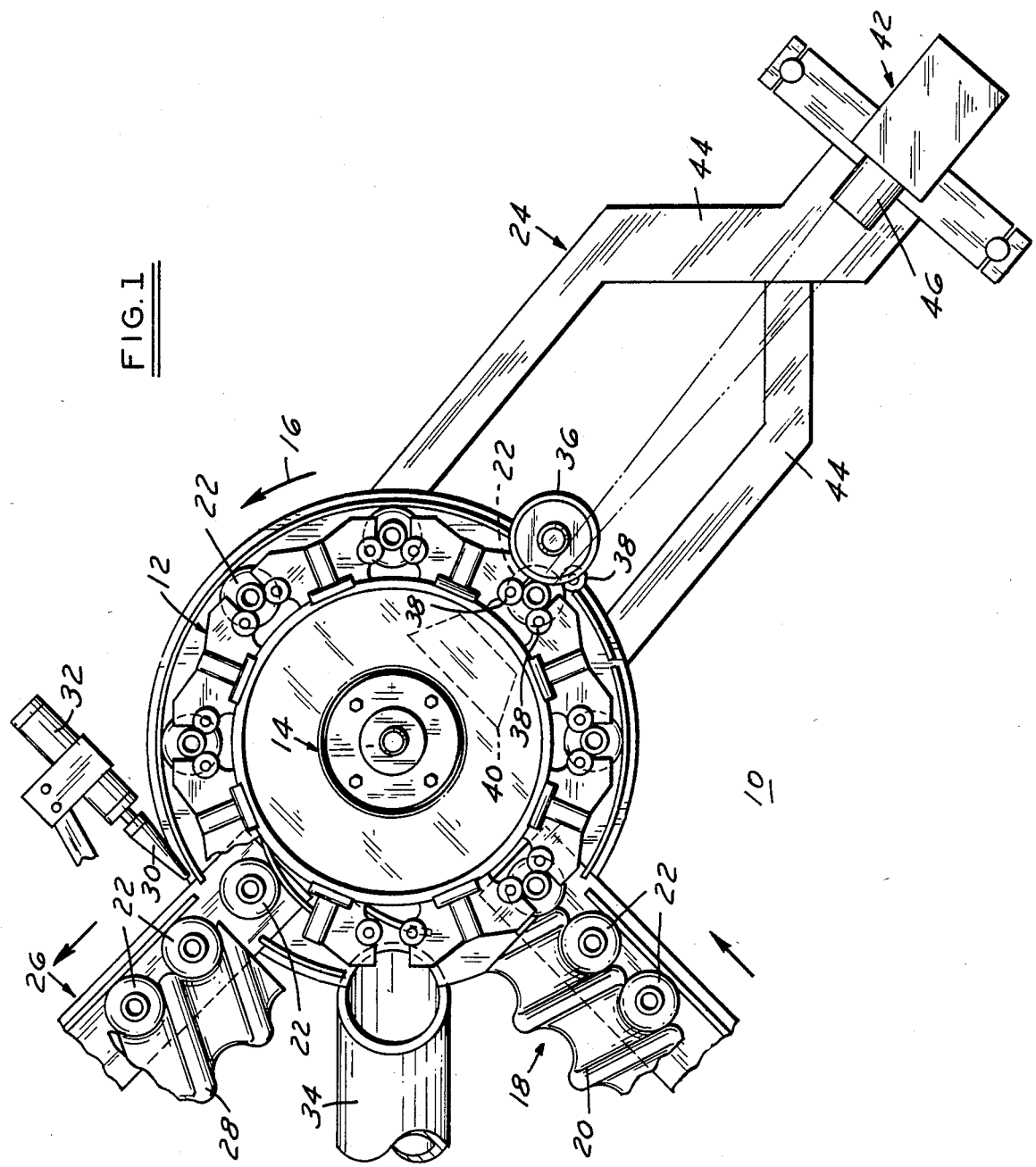
FIG. 1 is a plan view of a container inspection system in which the invention is employed.

FIG. 1 is a fragmentary plan view of a container inspection system 10 which includes a starwheel 12 coupled to a drive hub 14 for step-wise rotation in a counterclockwise direction indicated by the arrow 16. A feed conveyor 18 includes a driven screw 20 for feeding transparent containers 22 such as glass containers in upright orientation to the periphery of starwheel 12. Starwheel 12 conveys containers 22 in an arcuate path through a plurality of inspection stations, only one of which is illustrated in detail at 24. A discharge conveyor 26 includes a driven screw 28 which receives containers 22 from the periphery of starwheel 12 after each container has been moved by the starwheel through the plurality of inspection stations. A plunger 30 is coupled to a solenoid 32 and is disposed to block exit to discharge conveyor 26 when actuated by the solenoid 32. In the event that an unacceptable defect has been detected in a particular container at any of the inspection stations, plunger 30 is actuated to block exit to discharge conveyor 26 when that container is rotated to a position adjacent to such exit, so that the defective container is thereafter conveyed by starwheel 12 to a reject discharge chute 34.

The present invention relates to the inspection station which is illustrated at station 24. Station 24 includes a drive roller 36 positioned to engage a container 22 and to rotate the container in a counterclockwise direction while the container 22 is held in fixed axial position by the idler rollers 38. A light source 40 is positioned within the periphery of starwheel 12 beneath the plane of hub 14 so as to direct diffused light energy radially outwardly to provide illumination of the full height of the container sidewall while the container is rotated about its axis by drive roller 36. A camera 42 is positioned by the brackets 44 radially outwardly of light source 40 and starwheel 12. Camera 42 includes a linear array of light sensitive elements, i.e., pixles, preferably two hundred fifty-six, disposed in parallel alignment with the vertical axis of rotation of container 22 at station 24 and a lens 46 focuses a vertical strip of the sidewall of container 22 onto the element array. To the extent thus far described, inspection system 10 and inspection station 24 are similar to those disclosed in the aforementioned patents, and reference is made thereto for a more detailed description of the mechanical structure of the inspection system.

Light source 40 as disclosed in the aforementioned patents comprises a plurality of incandescent lamps disposed in three columns parallel to the axis of bottle rotation. A diffuser plate is positioned between the lamp array and the container to illuminate the entire container with a relatively wide angle source of uniform brightness. Lens 46 functions effectively to focus the linear array of camera 42 onto a vertical strip of the front portion of container 22. Sampling electronics receives signals from each pixel of the linear array of the camera 42 and provides strings of serial signals to an information processor which compares signals from adjacent pixels of the linear array in camera 42. The information processor provides an event signal when the signals from adjacent pixels differ by more than a preselected threshold level. The information processor electronics then operates solenoid 32 and plunger 30, when the associated defective container moves to the inspection station exit position, so that the defective container is sorted to the reject chute 34 as previously described. As indicated above, such inspecting and sorting technique has been quite effective and successful, but has encountered problems associated with distinguishing refractive defects from opaque defects. The present invention is directed toward solution of this difficulty.

FIG. 2 is an electro-optical schematic and functional block diagram of a presently preferred embodiment of the invention at inspection station 24. Within light source 40, which is illustrated in plan view in FIG. 2 (and in FIG. 1), the middle column or bank 48 of illumination lamps is connected directly to a source 49 of electrical power, while the outside columns or banks 50, 52 of illumination lamps are connected to power source 49 through a controlled electronic switch 54. Switch 54 may be of any suitable type. A diffuser plate 56 is positioned for directing illumination energy from lamp columns 48, 50, 52 through the sidewall of rotating containers 22 and through lens 46 onto the linear array of pixels (not shown) in camera 42. The sampling electronics 58 receives signals from each pixel within camera 42 and provides strings of serial signals to an information processor 60. Container 22 is rotated in the direction 61 at a substantially constant speed, and sampling electronics 58 is adjustable to provide a predetermined number, e.g., 300, of strings or scans per container depending on the speed of rotation. Information processor 60 generates an event signal when the magnitude of signals from adjacent pixels in a scan differ by more than a preselected threshold. It will be appreciated that the term "adjacent pixels" contemplates distinct elements which are in physical proximity to each other within the linear array of the camera 42. Information processor 56 performs a connectivity analysis by evaluating the locations of the event signals both "angularly" and longitudinally of the container to determine whether a defect is present. Based on the analysis, processor 60 controls operation of the solenoid 32 and the plunger 30 for sorting defective containers. Switch 54 in light source 40 receives a control signal from information processor 60.

In operation, successive containers 22 are conveyed to inspection station 24 by starwheel 12 (FIG. 1), held in position at the inspection station and rotated about their central axes. During a first such rotation, switch 54 is closed by information processor 60, so that all lamp banks 48, 50, 52 are energized and first diffused light energy is directed from a relatively wide source through the rotating container and through lens 46 onto camera 42, as illustrated schematically in plan view in FIG. 3A(1). Event signals (FIG. 3A(2)) are generated and stored in information processor 60 as previously described. The connectivity routine identifies an opaque defect as a tight cluster 69A (FIG. 3A(2)) of event signals, as distinguished from a loose cluster 69B which does not characterize an unacceptable opaque defect. The "tightness" of event signal clusters which should lead to a rejection is determined empirically by analyzing containers having known opaque defects, and by then adjusting processors 60 accordingly.

It would be appreciated in FIG. 3A(1) that an opaque defect at D blocks illumination of the camera along the path 69. While a refractive defect at D will effectively refract the camera field of view along the path 70A. Only a very large refractive defect will refract the camera field of view outside of the width of the light source in this first scan, so typical (but undesirable) refractive defects will appear transparent and not be detected. However, opaque defects are reliably detected in the manner described, and any container in which a defect is so detected will be rejected.

When container 22 has been rotated through one complete revolution, information processor 60 opens switch 54 so as to extinguish lamp banks 50, 52 as illustrated schematically in FIG. 3B(1). It will thus be appreciated that the effective width of the light source in FIG. 3B(1) is much narrower than was the case in FIG. 3A(1). Container 22 is then rotated through a second revolution, the pixel array in camera 42 is again sampled by electronics 58, and defect event signals are generated in information processor 60 as a function of a difference between adjacent pixel signals. A typical refractive defect at D will again refract the camera field of view, such as along the path 70A in FIG. 3B(1). However, because of the lesser effective width of the light source during this second scan, this refracted field of view will now appear dark. Thus, processor 60 may again perform a connectivity analysis of the event signals from adjacent pixels, and identify a defect from a close cluster of event signals. In FIG. 3B(2), clusters 70A(1) and 70A(2) illustrate small spaced refractive defects, which are commercially acceptable. Illustration 70A(3) illustrates a cluster of event signals which may result from a major horizontal blister.

Since all unacceptable opaque defects were identified and culled in the first scan (FIGS. 3A(1) and 3A(2)), defects detected in the second scan may be correctly associated with refractive defects. Thus, information processor 60 not only identifies and sorts containers having refractive and opaque defects, but also distinguishes between refractive and opaque defects. The latter information may be used for quality control purposes. It will also be noted from FIG. 3B(2) that a very minor refractive defect at D would only slightly refract the camera field of view, as along the path 70B, which is in within the source width, and thus would be invisible.

Figure 4:
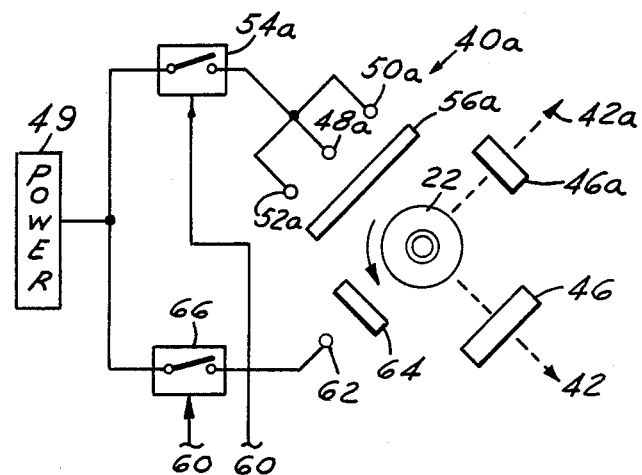
FIGS. 4 and 5 are fragmentary schematic diagrams illustrating respective alternative embodiments of the invention.

FIG. 4 is a fragmentary electro-optical schematic and functional block diagram illustrating an alternative embodiment of the invention. In the embodiment of FIG. 4, the light source 40a includes three columns or banks of lamps 48a, 50a and 52a parallel to the axis of rotation of container 49, and connected to power source 49 through a controlled switch 54a. Diffuser plate 56a is disposed between lamp banks 48a, 50a, 52a and the rotating container 22. A second controlled light source comprises a single column of lamps 62 parallel to the axis of container rotation and an associated diffuser plate 64. Diffuser plates 56a and 64 are at an angle with respect to each other with respect to the axis of the field of view of lens 42. Lamp bank 62 receives power from source 49 through a controlled switch 66. Switches 54a and 66 receive control signals from information processor 60 (FIG. 2). Each lamp/diffuser plate combination has associated therewith a diametrically opposed lens 46, 46a and camera 42, 42a (not shown). During a first inspection scan of container 22 at station 24a, switch 54 is closed and switch 66 is opened so that container 22 is illuminated effectively by a wide light source comprising lamp banks 48a, 50a and 52a. Such light energy is transmitted through the sidewall of container 22 and directed by lens 46 onto camera 42 (FIG. 2), and appropriate defect event signals are generated as previously described. Lamp banks 48a, 50a and 52a are then extinguished by opening switch 54a, and lamp bank 62 is energized by closure of switch 66 so as to illuminate container 22 during a second scan from a narrower light source. Defect event signals are generated as previously described.

Figure 5:
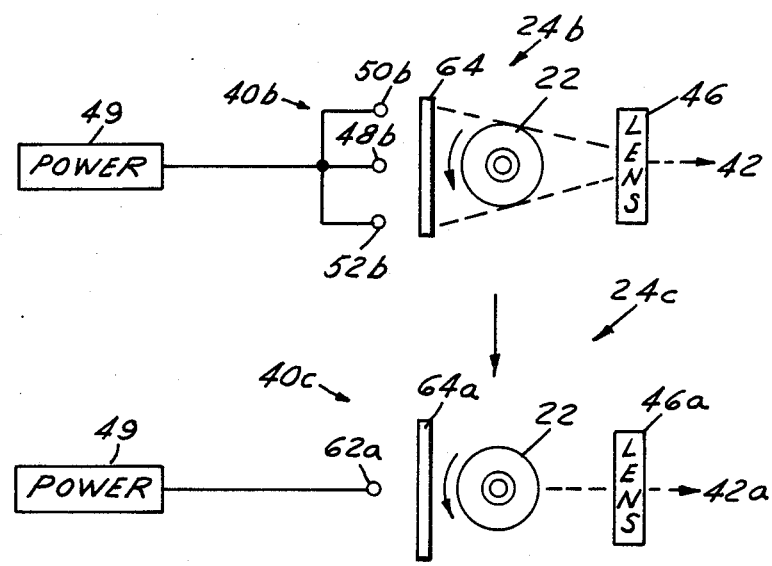

FIG. 5 illustrates a third embodiment of the invention wherein separate light sources 40b and 40c are positioned at respective separate inspection stations 24b, 24c in the path of rotation of starwheel 12 (FIG. 1). Wide light source 40b includes three banks 40b, 50b and 52b of illumination lamps connected to the power source 49. A relatively wide source of diffuse illumination is thus directed onto container 22 at station 24b and appropriate defect event signals are generated. Container 22 is then conveyed by the starwheel 12 (FIG. 1) to station 24c wherein a single column or bank 62a of illumination elements is connected to power source 49. Diffused illumination is thus directed for a narrow source through container 22, and corresponding defect event signals are generated as previously described herein. The embodiments of FIGS. 4 and 5 have the disadvantage of requiring two cameras 42 and lenses 46, but otherwise are equivalent to the more preferred embodiment of FIGS. 2 and 3.

Sampler electronics 58 and information processor 60 (FIG. 2) are disclosed in greater detail in the aforementioned U.S. Pat. Nos. 4,378,494 and 4,378,495. The only modifications required to the circuits so disclosed are the addition of control circuitry for operating switches 54, 54a and/or 66 (FIGS. 2 and 4). Implementation of such modifications will be self-evident to the artisan in view of the foregoing discussion.

I claim:

1. A method of sorting transparent containers having defects in the container sidewalls, which defects affect optical transmission characteristics of the container sidewalls, said method comprising the steps of:
   (a) sequentially directing first and second sources of diffused illumination onto the sidewall of a container while rotating the container about its central axis, said sources having differing widths transversely of said axis,
   (b) monitoring light energy transmitted by each of said first and second sources through the container sidewall as a function of container rotation,
   (c) identifying defects in the container sidewall as a function of light energy transmitted by each of said first and second sources through the container sidewall, and
   (d) rejecting a container in which a defect is so identified, whereby a defective container is sorted from commercially acceptable containers.

2. The method set forth in claim 1 wherein said step (b) comprises the step of positioning camera means which includes a plurality of light responsive elements disposed in at least one linear array parallel to said axis, and
   wherein said step (c) comprises the step of identifying defects in the container sidewall as a function of differences in light energy sensed by adjacent ones of said elements from each of said light sources.

3. The method set forth in claim 2 wherein said step (a) comprises the step of (a1) providing a plurality of light source means disposed in an array which extends laterally of said axis, and (a2) selectively energizing said light source means to provide said first and second sources of illumination.

4. A method of sorting transparent containers having defects in the container sidewalls, which defects affect optical transmission characteristics of the container sidewalls, said method comprising the steps of:
   (a) rotating a said container about its central axis,
   (b) positioning camera means adjacent to the rotating container, said camera means including a plurality of light sensitive elements disposed in at least one linear array having a field of view parallel to said axis, (c) directing a first source of diffused illumination onto said container sidewall, said first source being sufficiently wide transversely of said axis that said field of view through a refractive defect in said sidewall is within said source, an opaque defect in said sidewall blocking illumination from said source to said camera means, (d) directing a second source of diffused illumination onto said container sidewall, said second source being sufficiently narrow transversely of said axis that said field of view through a refractive defect in said sidewall is outside of said second source, (e) identifying opaque defects in the container sidewall as a function of differences in illumination sensed by adjacent ones of said elements in said array from said first source, (f) identifying refractive defects in the container sidewall as a function of differences in illumination sensed by adjacent ones of said elements in said array from said second light source, and (g) rejecting a container in which either an opaque defect or a refractive defect is so identified, whereby a defective container is sorted from commercially acceptable containers.

5. The method set forth in claim 4 comprising the additional step of distinguishing among types and sizes of defects in the container sidewall as a function of said differences in said steps (e) and (f), and wherein said rejecting step (g) includes the steps of rejecting containers having selected types and sizes of sidewall defects while accepting containers having other types and sizes of sidewall defects.

6. Apparatus for detecting defects in the sidewall of transparent containers and sorting containers having such defects, comprising first and second light source means for providing respective first and second diffused illuminations, means for positioning a container adjacent to said light source means sequentially to illuminate the container sidewall, sensing means positioned to sense the diffused illumination provided by said light source means by viewing both said first and second source means sequentially through the illuminated container sidewall, said light source means being generally transverse to the line-of-sight of said sensing means, said first light source means being wider transversely of said line-of-sight than said second light source means and of sufficient width so that said sensing means views said first light source means when the line-of-sight of said sensing means is refracted by a defect, means for identifying such refractive defect in a container when the line-of-sight of said sensing means is refracted outside the width of said second light source means during said second illumination but within the width of said first light source means during said first illumination, and means for rejecting a container in which such refractive defect is so detected.

7. The apparatus set forth in claim 6 wherein said sensing means comprises a plurality of light responsive elements disposed in at least one linear array parallel to the axis of a container rotated by said positioning means, and wherein said identifying means includes means responsive to differences in light energy received at adjacent said elements.

8. The apparatus set forth in claim 6 wherein said light source means comprises a plurality of lamp means disposed in an array parallel to the axis of a container rotated by said positioning means, and means for selectively energizing said plurality of lamp means.

9. The apparatus set forth in claim 8 wherein said light source means comprises a plurality of lamps disposed in multiple columns parallel to said axis, and wherein said selective energizing means comprises means for selectively energizing said lamp columns.

10. The apparatus set forth in claim 9 wherein said light source means comprises three columns of lamps, the center column being aligned with said camera means and said axis and the outside columns being disposed at opposite angles to said axis and said camera means, and wherein said selectively energizing means comprises means for selectively energizing said outside lamp columns to provide said second illumination having narrow illumination width when only said center column is energized and said first illumination of greater width when all three of said columns are energized.

11. The apparatus set forth in claim 8 wherein said light source means comprises first and second dissimilar banks of lamps disposed adjacent to said positioning means, and wherein said selective energizing means comprises means for selectively energizing said first and second lamp banks.

12. The apparatus set forth in claim 6 further comprising conveyor means for feeding containers sequentially to and from said positioning means, and means for selectively activating said rejecting means to direct containers from said conveyor means when a said defect is detected.

13. The apparatus set forth in claim 12 comprising first and second dissimilar light source means, first and second sensing means, and first and second positioning means disposed at spaced stations in said conveyor means.

* * * * *